United States Patent
Schaffrath et al.

(10) Patent No.: US 7,776,000 B2
(45) Date of Patent: Aug. 17, 2010

(54) NON-INVASIVE SYSTEM FOR FIXING NAVIGATIONAL REFERENCE

(75) Inventors: Claus Schaffrath, Munich (DE); Gerhard Kleinszig, Buch (DE); Christoph Schenkel, Puchheim (DE)

(73) Assignee: BrainLAB AG, Feldkirchen (DE)

( * ) Notice: Subject to any disclaimer, the term of this patent is extended or adjusted under 35 U.S.C. 154(b) by 971 days.

(21) Appl. No.: 11/170,974

(22) Filed: Jun. 30, 2005

(65) Prior Publication Data

US 2006/0041206 A1   Feb. 23, 2006

Related U.S. Application Data

(60) Provisional application No. 60/588,820, filed on Jul. 16, 2004.

(30) Foreign Application Priority Data

Jun. 30, 2004   (EP)   .................................. 04015307

(51) Int. Cl.
*A61F 5/00* (2006.01)
*A61B 5/05* (2006.01)
*A47B 13/00* (2006.01)

(52) U.S. Cl. .............................. 602/26; 600/424; 5/601

(58) Field of Classification Search ................. 128/870, 128/869; 5/601, 689, 702, 911, 913, 630, 5/706–715; 600/407, 410, 414, 415, 416, 600/421–422, 425, 424, 426–428; 381/128, 381/130, 131, 132; 602/6

See application file for complete search history.

(56) References Cited

U.S. PATENT DOCUMENTS

| 3,762,404 | A | 10/1973 | Sakita |
| 5,626,150 | A * | 5/1997 | Johnson et al. ................. 5/628 |
| 5,945,827 | A * | 8/1999 | Gronauer et al. ............ 324/318 |
| 6,241,735 | B1 | 6/2001 | Marmulla |
| 2002/0188194 | A1 | 12/2002 | Cosman |
| 2004/0199072 | A1* | 10/2004 | Sprouse et al. .............. 600/424 |
| 2005/0080332 | A1* | 4/2005 | Shiu et al. .................... 600/411 |
| 2005/0251914 | A1* | 11/2005 | Schaller et al. ................ 5/601 |

FOREIGN PATENT DOCUMENTS

DE   102 06 166 A1   8/2003

OTHER PUBLICATIONS

European Search Report for corresponding Application No. 04015307.4 dated Dec. 8, 2004.

* cited by examiner

*Primary Examiner*—Patricia M Bianco
*Assistant Examiner*—Tarla R Patel
(74) *Attorney, Agent, or Firm*—Renner, Otto, Boisselle & Sklar, LLP

(57) ABSTRACT

A fixing system and method for fixing a navigational reference array for image-assisted medical treatment with respect to a patient, wherein the reference array is arranged the patient's body with the assistance of an immobilizing device, and wherein the immobilizing device is a vacuum mattress or a vacuum mattress patient jacket, and at least one anchoring for the reference array is provided on or in the vacuum mattress or a vacuum mattress patient jacket.

11 Claims, 1 Drawing Sheet

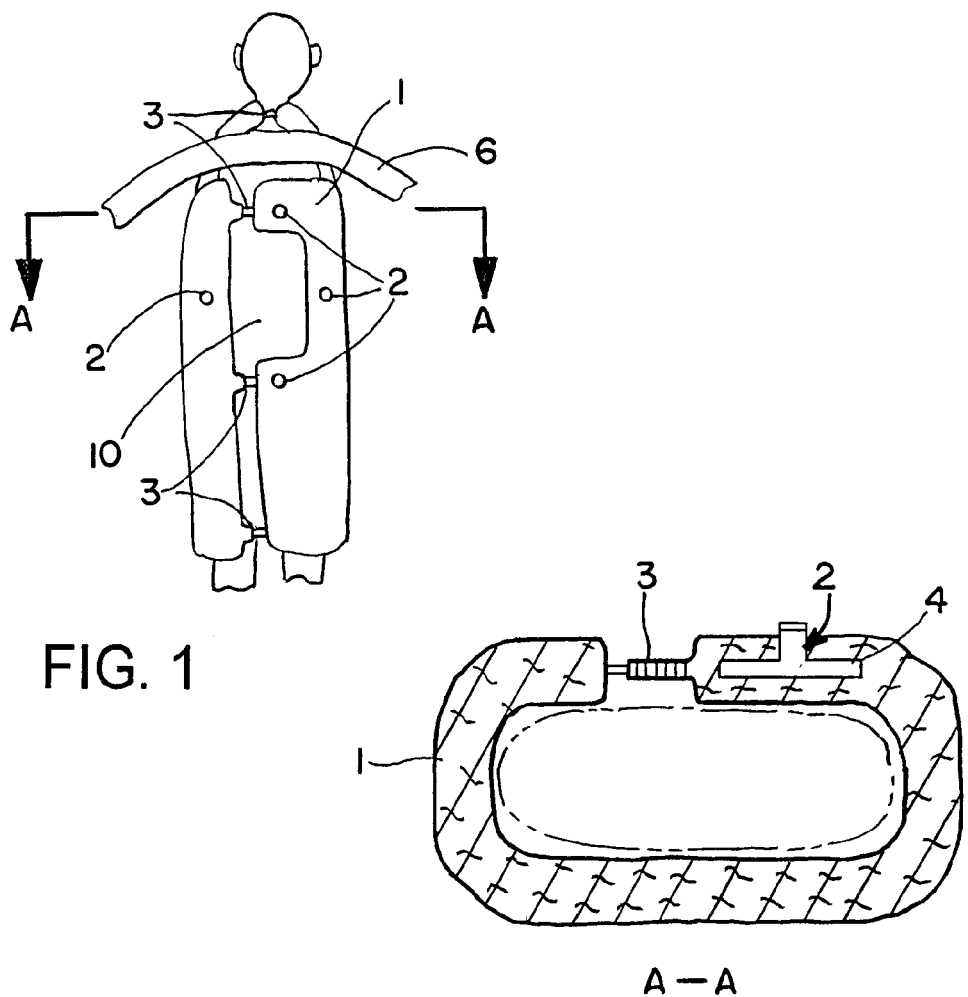
FIG. 1
FIG. 2
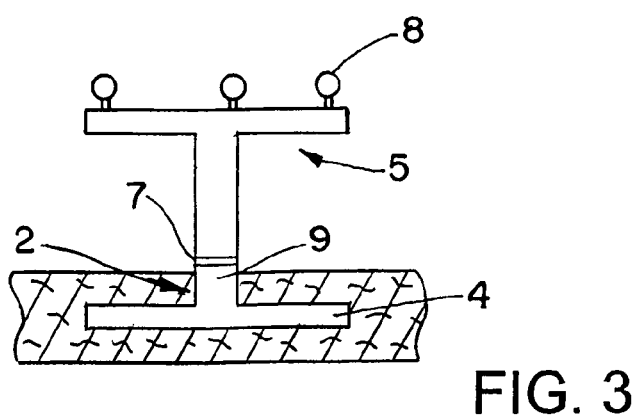
FIG. 3

NON-INVASIVE SYSTEM FOR FIXING NAVIGATIONAL REFERENCE

RELATED APPLICATION DATA

This application claims priority of U.S. Provisional Application No. 60/588,820 filed on Jul. 16, 2004, which is hereby incorporated herein by reference in its entirety.

FIELD OF THE INVENTION

The present invention relates to non-invasively fixing a navigational reference which can be positionally determined and tracked by a localizing system of a medical navigation system. More particularly, the invention relates to the field of intra-operative navigation with non-contact registering of the reference or reference array, respectively, specifically for applications in the spinal area.

BACKGROUND OF THE INVENTION

In medical navigation, a patient reference or reference array is fixed with respect to a part of the body to be treated. In the area of spinal treatment, for example, this conventionally has been achieved by attaching the reference array to an exposed section of bone and then registering, i.e., positionally assigning, the reference array in a navigation system. A disadvantage of such conventional methods is that in order to gain access to the section of bone (e.g. vertebra) to which the reference array is to be attached, relatively large incisions into the skin and through the tissue must be performed. In cases where the actual surgery can be performed using a thin and/or small instrument, the problem then arises that attaching the reference array represent the most invasive aspect of the entire treatment.

A localizing device for determining the position of a patient is known from DE 102 06 166 A1, wherein a vacuum mattress is used to place the patient. A box-like couch, which includes two side walls that stand up on both sides of the patient, is placed around the vacuum mattress and the patient. Navigational markings are arranged on the sidewalls, and the patient is immobilized and fixed with respect to the markings. A disadvantage of this is approach is that the patient and/or the area to be treated is relatively far from the markings, which can reduce the accuracy of the navigation. Also, the proposed box-like arrangement is very bulky and difficult to handle, and can obstruct the area to be treated.

DE 197 31 040 A1 describes a device and a method for fixing parts of a body, wherein a patient is positioned on a bearing surface and then covered with a foil. The patient is immobilized by suctioning air from under the foil, thereby collapsing the foil around the patient. The reference, as a secondary aspect, also describes how holding arms can be used that include a base beneath the foil, wherein the holding arms pass through the foil and are attached at the other end to the patient couch. The holding arms are designed with joints and are attached both to the patient and to the couch only via the suctioning effect created by the partial vacuum. DE 197 31 040 A1 also proposes attaching a marker system to the holding arms. However, attaching the holding arms via the foil and partial vacuum may not offer a sufficient holding force to rigidly fix such markings with respect to the patient. As a result, accuracy in navigation can be affected. Further, due to the holding arm joints and the unstable fixing by means of the foil, a fixed arrangement of such markings with respect to the parts of the body cannot be ensured.

SUMMARY OF THE INVENTION

The present invention relates to a fixing system for fixing a navigational reference device for image-assisted medical treatment with respect to a patient, so as to enable one to treat a patient with navigational assistance. Data on the patient's body structure, captured beforehand, can be visibly displayed in its correct positional relation with respect to instruments or other treatment means. The reference device, which is arranged in a fixed position with respect to the part of the patient's body, provides reference data to the navigation system. The data can be used by the navigation system to display the location of a treatment instrument and/or body structure in real time.

In accordance with the present invention, a fixing system includes a reference device that can be arranged outside the patient's body. An immobilizing device, such as a vacuum mattress or a vacuum mattress patient jacket, includes at least one anchor point (also referred to as an anchor) for the reference device, wherein the reference device can be attached directly to the immobilizing device. By attaching the reference device to the immobilizing device, the location of the reference device relative to the area to be treated can be ensured. Further, since the reference device can be attached to the immobilizing device (as opposed to the area to be treated), the reference device does not obstruct the area to be treated. Additionally, since the immobilizing device can be a vacuum mattress or a vacuum mattress patient jacket, which, once evacuated, is completely rigid, a stable and immovable location can be provided for fixing the reference device with respect to the patient. For at least this reason, it is sufficient to provide one anchor point for the reference device; on which the reference device can then be fixed.

In a preferred embodiment of the present invention, the anchor point includes a base, e.g. base plate, (the base need not necessarily be rigid, but can also be made of a flexible material and become rigid during evacuation) which can be rigidly fixed in a known position with respect to the immobilizing device when the immobilization device is evacuated. Such a base can ensure a sufficient hold in order to provide a rigid and stable anchor point. The base can be embedded within filling material of the immobilizing device and can include a connection to the reference device. The connection can protrude to the outer side of the immobilizing device through a sealed, air and/or gas-tight opening. This arrangement in the interior of the immobilizing device can ensure that following evacuation, the base is held firmly in place.

The reference device can be integrally formed with the connection and the base. It also is possible to form the reference device as a separate component, such that the reference device can be placed onto the connection via an adaptor. This arrangement allows very simple handling and provides the option of only attaching the reference device when it is needed, e.g., after immobilizing the patient and/or shortly before or during treatment.

A number of anchor points may be provided at spaced locations on the immobilizing device. This enables the patient to be immobilized via the immobilizing device, and a reference device to then be placed on one of the anchor points. The reference device can be attached, for example, using a plug connection, latch connection, threaded connection or other detachable connection. Preferably, the reference device can be attached to an anchor point that is as near as possible to the part of the patient's body to be treated or operated on. By providing a number of anchor points at spaced and likely suitable locations, e.g., in the peripheral area of the immobilizing device, a location near the area to be treated typically can found. Accordingly, the immobilizing device can be used for a number of different treatments or procedures.

In addition, using an immobilization device such as a vacuum mattress or vacuum mattress patient jacket also offers another advantage. Such immobilizing devices can be freely configured in their shape, such that in accordance with one aspect of the invention, it is possible to provide at least one recess or transit window that allows access to parts of the patient's body in need of treatment. It is thus possible on the one hand to effectively immobilize the patient and fixedly anchor the reference device, and on the other to achieve optimum access to the region of the patient to be treated. It is advantageous if the anchor points are arranged around the periphery of the transit window, in order to place them in the vicinity of the treatment location.

The immobilizing device may be dimensioned such that it can envelope the torso area of the patient, wherein it can be pre-fixed to the patient with the aid of clasps on its peripheral areas, before the patient is conclusively immobilized by evacuating the mattress.

In the following, the invention is explained in more detail on the basis of a preferred embodiment. The features of the invention cited in this description can be implemented individually and in any combination.

BRIEF DESCRIPTION OF THE DRAWINGS

FIG. 1 illustrates a schematic view from above a patient who has been immobilized using a vacuum mattress jacket including a fixing system in accordance with the invention.

FIG. 2 is a view of the section A-A in FIG. 1.

FIG. 3 illustrates a reference device including a base that can be used with the fixing system in accordance with the invention.

DETAILED DESCRIPTION

FIG. 1 illustrates a patient in a face-down position, on whom an operation is to be performed in the vertebral area. The patient is held on a couch (not shown) with the aid of a strap 6. In the present example, it is noted that in accordance with the present invention, the patient need not necessarily be fixed in a completely rigid manner. This is due to the fact that the patient is enclosed by a vacuum mattress patient jacket which bears the reference numeral 1. A plurality of anchor points 2 for securing a plurality of navigational reference devices (illustrated in FIG. 3 as exemplary reference arrays 5) are provided on vacuum mattress patient jacket 1. The patient can therefore only move together with the jacket 1, and since the reference arrays 5 in the anchor points 2 would move with the jacket 1, the corresponding movement is taken into account by the navigation system and, thus, no errors arise. It is therefore unnecessary to completely fix the patient on the couch. Only the anchor points 2 (and therefore the reference arrays) cannot move with respect to the patient. Maintaining the anchor points 2 in a fixed relation is ensured by the fixed vacuum mattress jacket, thus allowing some patient movement. Accordingly, the patient is substantially more comfortable than when completely immobilized.

The vacuum mattress jacket 1 envelopes the patient in the torso area and can be pre-fixed using clasps 3 before the air is suctioned off from the jacket's interior. In the embodiment shown, the jacket 1 includes a window 10 which ensures access to the area of operation.

At this point, it is noted that it is not absolutely necessary to provide such a jacket. In some cases, it can be sufficient to immobilize the patient simply by placing the patient onto a vacuum mattress (not shown), wherein the vacuum mattress includes anchor points for attaching reference arrays at locations next to the patient.

In the case shown, however, the patient is enveloped in the torso area, and FIG. 2 shows section A-A in FIG. 1, from which it is clear how the anchor point 2 is inserted within filling material (not shown) of the jacket 1. A clasp 3 can also be seen in FIG. 2.

The anchor point 2 in FIG. 2 is the same as that which can be seen in FIG. 3 and includes a base plate 4 and a connection or connection section 9. The base plate 4 is embedded within the filling material of the vacuum jacket 1 (or vacuum mattress), wherein the connection section 9 protrudes upwards out through the upper material of the jacket 1. The resultant opening in the jacket is sealed using an air or gas-tight seal. By embedding the base plate 4, it is enveloped on all sides by the filling material of the jacket 1 and rigidly fixed once the jacket has been evacuated. Rigidly fixing the base plate 4 with respect to the jacket 1 and, therefore, with respect to the patient, ultimately leads to the reference array 5 being rigidly and immovably fixed with respect to the parts of the patient's body to be treated.

On its upper side, the reference array 5 includes, for example, three markers 8. The markers can be reflective passive markers that can be detected using infrared cameras. Markers for visible light also can be used, or markers which passively or actively indicate their position within electrical or magnetic fields. Each of the above markers 8 can be localized by the navigation system. Navigation systems are well known in the art and will not be discussed herein. Further information regarding medical navigation systems can be found in U.S. Patent Publication No. 2003/0225329, which is hereby incorporated by reference.

In the present example, the reference array 5 is placed onto the connection section 9 of the base 2 via a connector 7 (adaptor), resulting in a rigid and immovable mount. The adaptor 7 is shown only schematically; any positionally fixed plug connection, threaded connection, latch connection or similar type of connection can be utilized for the adapter.

As can be seen again from FIG. 1, the anchor points 2 in the present example are arranged around the window 10, such that they are situated in the vicinity of the treatment location and therefore enable precise navigation of the area to be treated. The present invention allows a navigational reference device or reference array to be stably and reliably fixed with respect to the patient, without requiring invasive surgery to attach the navigational reference device or reference array to the area to be treated. Using the present invention, and with highly precise navigational assistance, minimally invasive operations can be performed, particularly in the spinal area, e.g., administering injections in the intervertebral area, or using vertebroplasty in which cannulae have to be positioned in order to introduce supporting mass into vertebrae. However, the invention is also suitable for any other applications in which minimal invasive surgery is performed.

In conclusion, it is noted that when using the invention intra-operatively, the base of a reference array attached in accordance with the invention is advantageously registered in the navigation system in a non-contact process. It is then advantageous if a material is used for the jacket 1 and filling material which is permeable to x-rays, since in such cases, the base can be registered in a non-contact process via x-ray C-arcs, navigation systems with fluoro-to-CT or fluoro-to-MR registration or via 3D C-arcs which produce three-dimensional images from a number of individual recordings.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A fixing system for fixing a navigational reference device for image-assisted medical treatment with respect to a patient, wherein said navigational reference device is arranged outside the patient's body, comprising:
    an immobilization device; and
    at least one anchor point in or on the immobilization device, said anchor point couplable to the navigational reference device, and
    wherein said immobilization device is a vacuum mattress or a vacuum mattress patient jacket.

2. The fixing system as set forth in claim 1, wherein said anchor point comprises a base which is rigidly fixed in a known position with respect to the immobilization device when the immobilization device is evacuated.

3. The fixing system as set forth in claim 2, wherein said base is embedded within a filling material of the immobilization device and said anchor point further comprises a connection section,
    wherein said connection section protrudes through the filling material to an outer side of the immobilization device via an opening which is sealed air-tight and/or gas-tight.

4. The fixing system as set forth in claim 3, wherein the navigational reference device is integrally formed with said connection section and the base.

5. The fixing system as set forth in claim 3, wherein the navigational reference device is formed as a separate component and can be placed onto the connection section via an adaptor.

6. The fixing system as set forth in claim 1, wherein a number of anchor points are provided at spaced locations on the immobilization device.

7. The fixing system as set forth in claim 1, wherein immobilization device comprises at least one recess or transit window that allows access to parts of the patient's body in need of treatment.

8. The fixing system as set forth in claim 7, wherein the anchor points are arranged around the periphery of the transit window.

9. The fixing system as set forth in claim 1, wherein the immobilization device is dimensioned such that it can envelope a torso area of the patient, wherein the immobilization device is pre-fixed with the aid of clasps on peripheral areas of the immobilization device.

10. A method for fixing a navigational reference for image-assisted medical treatment with respect to a patient, wherein the navigational reference is located outside the patient's body, comprising the steps of fixing a vacuum mattress or a vacuum mattress patient jacket to the patient, and attaching a navigational reference to an anchor on or in the vacuum mattress or a vacuum mattress patient jacket.

11. The fixing system as set forth in claim 1, further including the navigational reference device.

* * * * *